United States Patent [19]

Fajula et al.

[11] Patent Number: 4,891,200

[45] Date of Patent: Jan. 2, 1990

[54] OMEGA TYPE ZEOLITE HAVING HIGH THERMAL STABILITY, ITS PROCESS OF PREPARATION AND ITS UTILIZATION

[75] Inventors: François Fajula, Teyran; François Figueras, Montpellier, both of France; Latifa Moudafi, Djemaa Casablanca, Morocco; Mercedes Vera Pacheco, Mexico City, Mexico; Serge Nicolas, Montpellier, France; Pierre Dufresne, Rueil Malmaison, France; Claude Gueguen, Septeme Pont Eveque, France

[73] Assignees: Centre National de la Recherche Scientifique, Elf France, Paris; Institut Francais du Petrole, Rueil Malmaison Cedex, both of France

[21] Appl. No.: 865,179

[22] Filed: May 19, 1986

[30] Foreign Application Priority Data

May 23, 1985 [FR] France ............................ 85 07772

[51] Int. Cl.$^4$ ............................................. C01B 33/28
[52] U.S. Cl. .................................... 423/328; 423/118
[58] Field of Search ................ 423/118, 328 Z, 328 T, 423/329, 328

[56] References Cited

U.S. PATENT DOCUMENTS

| | | | |
|---|---|---|---|
| 3,185,544 | 5/1965 | Maher | 423/118 |
| 3,414,602 | 12/1968 | Acara | 423/328 T |
| 3,578,723 | 5/1971 | Bowes et al. | 423/328 T |
| 3,914,331 | 10/1975 | Lucki et al. | 208/120 |
| 3,923,639 | 12/1975 | Ciric | 208/120 |
| 3,947,482 | 3/1976 | Albers et al. | 502/77 |
| 4,021,447 | 5/1977 | Rubin et al. | 423/328 T |
| 4,091,007 | 5/1978 | Dwyer et al. | 556/173 |
| 4,241,036 | 12/1980 | Flanigen et al. | 502/62 |
| 4,552,731 | 11/1985 | Vaughan | 423/118 |

FOREIGN PATENT DOCUMENTS

| | | | |
|---|---|---|---|
| 0127399 | 12/1984 | European Pat. Off. | 502/77 |
| 1117568 | 6/1968 | United Kingdom | 423/328 T |
| 2101110 | 1/1983 | United Kingdom | 423/328 T |

OTHER PUBLICATIONS

V. Penchev et al, "Thermochemical and Acidic Properties of the Zeolites Offrelite, omega and ZSM-5" *Zeolites* vol. 3, No. 3 Jul. 1983 pp. 249–254.

V. Mavrodinova, "Toluene inversion on the zeolites offretite, omega and ZSM-5" *Zeolites* vol. 5, No. 4, Jul. 1, 1985 pp. 217–221.

Lok et al, "The Role of Organic Molecules in Molecular Sieve Synthesis", *Zeolites*, v. 3, pp. 282–291 (Oct. 1983).

Francis G. Dwyer et al, "ZSM-4 Crystallization via Faujasite Metamorphosis", *Journal of Catalysis*, 59 (263–271) (1979).

A. J. Perrotta, J. of Catalysis 55, pp. 240–249 (1978).

Barrer and al., J. Chem. Soc. 971 (1961).

E. Galli and al., Contrib. Mineral Petrology 1974, 45(2) (99–105).

J. F. Cole, Advan. Chem. Ser. 1973, 583–595.

*Primary Examiner*—John Doll
*Assistant Examiner*—R. Bruce Breneman
*Attorney, Agent, or Firm*—Burgess, Ryan and Wayne

[57] ABSTRACT

This invention concerns an omega type zeolite of high thermal stability, present in the form of hexagonal prismatic monocrystals having scored or plane faces of 0.1 $\mu$m in edge and 0.5 to 5 $\mu$m in length, this zeolite being obtained through crystallization from a mother solution containing a silica source, alumina, metallic oxide, an organic cation and water, in which the alumina source is a crystalline aluminosilicate of which at least one part is in suspension in the mother solution. In its acid form this zeolite can be used as catalyst for hydration of olefins and isomeric change of xylenes.

20 Claims, 1 Drawing Sheet

OMEGA TYPE ZEOLITE HAVING HIGH THERMAL STABILITY, ITS PROCESS OF PREPARATION AND ITS UTILIZATION

BACKGROUND OF THE INVENTION

1. Field of the Invention

The present invention concerns an omega type zeolite having high thermal stability, its process of preparation and its utilization.

Zeolites are hydrated crystalline silicoaluminates having the following general formula:

$$M_{2/n}O; Al_2O_3; xSiO_2; yH_2O$$

where:

M is a cation of valency n;

x and y numbers higher than 1.

The crystalline structure of the zeolites is comprised of $AlO_4$ and $SiO_4$ tetrahedra, connected between one another by oxygen atoms common to the two tetrahedra. The tetrahedra surround cage or channel shaped cavities, occupied by metallic ions and water molecules.

Through ion exchange and dehydration it is possible to set free about 50% of the total volume.

In the microporous materials thus obtained, the channels and cages have variable forms and dimensions, that determine the size of the molecules that can be adsorbed and desorbed by a given zeolite during its utilization as catalyst or for the separation of molecules.

Synthetic zeolites, which allow the adaptation of the size and the form of the cavities to well defined syntheses, or the separation of specific molecules, currently assume increasing importance.

Currently, of the 36 natural zeolites known about one third can be synthesized.

For the reactions of hydrocarbonated molecules encountered in the petrochemical industry, it is necessary to dispose of zeolites comprising pores large enough to allow the adsorption and the desorption of bulky molecules.

2. Description of the Prior Art

The synthesis of zeolites consists in crystallization of over-saturated alkaline solutions of freshly precipitated alumina and silica gels. The synthesis is performed in the presence of mineral cations (most frequently from among group I of the Periodic Table of Elements) and/or organic cations, generally of the tetraalkylammonium type {Barrer and al., J. Chem. Soc. 971 (1961)}.

U.S. Pat. No. 4,241,036 assigned to UNION CARBIDE discloses the synthesis of a large-pore zeolite through crystallization of an alkaline aluminum hydroxide solution and a silica gel in the presence of tetramethylammoniums. This zeolite called omega zeolite has a natural equivalent, called mazzite (E. Galli and al., Contrib. Mineral Petrology 1974, 45 (2) 99-105).

However, despite its structure comprising large pores, omega zeolite has not until now been successfully used on an industrial scale and the lack of interest in its use and application is due to its poor thermal stability.

The poor resistance to temperature of this zeolite is due to its proper composition. The tetraalkylammonium ions, trapped in the structure, cannot be eliminated by currently used exchange methods. Their elimination requires a heat treatment at temperatures higher than 500° C., known as calcination.

When this treatment is performed in the presence of an inert gas, the decomposition of the tetraalkylammonium cations leads to a carbon deposit, thus to a drop in activity. In the presence of air or oxygen, carbon deposits can be prevented, but the exothermicity of the oxidation reaction of these cations creates hot sites in the structure. This results in the partial destruction of the network, thereby provoking a loss of porous volume, rendering fragile the whole of the structure (J. F. Cole, Advan. Chem. Ser. 1973, 583).

The limit temperature to which the zeolite can be subject in a calcination treatment under air measures its regenerating capacities during its use in an industrial process. The low thermal stability of the zeolite limits regenerating possibilities, and renders difficult, and even impossible its industrial use.

SUMMARY OF THE INVENTION

It has been observed in an unexpected way that by replacing the very pure amorphous alkaline aluminates by crystalline aluminosilicates which may be even less pure, as the alumina source, the omega zeolite is obtained in the form of large uniform crystals having very good thermal stability.

With respect to the amorphous alumina sources used in the prior art, the crystalline aluminosilicate has a lower dissolution speed, which allows one to control the growth speed of the omega zeolite crystals. A slower crystallization is favorable to the formation of large uniform crystals. Furthermore, the growth of the zeolite is oriented by the epitaxy phenomenon observed between the zeolite and the aluminosilicate leaves. The epitaxy phenomenon is discernible when the reaction is interrupted prior to complete zeolitization and can be obtained for the whole of the zeolites of hexagonal structure (offretite, erionite, omega and L zeolite) on numerous crystalline aluminosilicates. The zeolites according to the invention are produced with a crystal growth speed lower than 9 g/h for 100 ml of mixture and preferably lower than 1 g/h.

The synthesis process of the omega zeolite according to the invention consists in causing the zeolite to crystallize from a mother solution containing a silica source, an alumina source, a metal oxide, an organic cation and water, in the molar ratios comprised between:

$$1.25-16M_{2/n}O; 0.01-1Z_2O; Al_2O_3; 5-40SiO_2; 80-640H_2O$$

where:

M is a metal of valency n; and

Z is an organic cation, wherein the alumina source is a crystalline aluminosilicate of which at least one part is in suspension in the mother solution. The size of the particles of the crystalline aluminosilicate in suspension is comprised between 0.5 and 100 μm and preferably between 1 and 10 μm.

By comparing the appearance of the crystals determined by electronic scanning microscopy, of an omega zeolite obtained according to the invention and an omega zeolite obtained from an amorphous alumina source, a great difference in their macrocrystalline structure is observed.

The omega zeolite obtained from an amorphous alumina source is present in the form of beads and irregular rods or sticks {A. J. Perrotta, J. of Catalysts 55, 250 (1978)}.

This zeolite loses its crystallinity at a temperature of about 800° C.

The omega zeolite prepared according to the invention is distinguished by the size and the form of its crystals. It is present in the form of hexagonal prismatic monocrystals having scored or plane faces of 0.1 to 5 µm edge and from 0.5 to 5 µm length.

Figure 2:
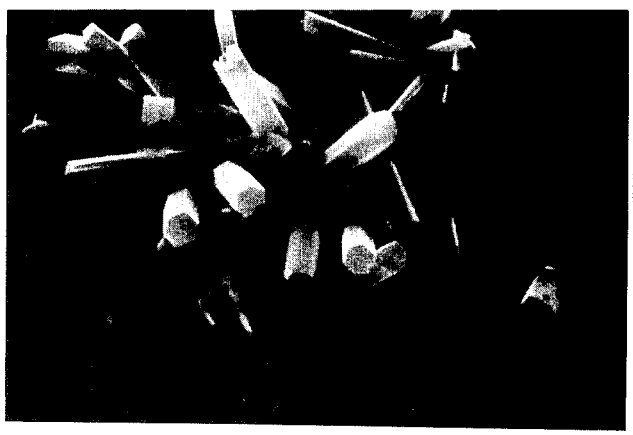

FIG. 2 represents the microphotography (enlargement 12,500) of the omega zeolite prepared from non calcinated kaolin, according to the operating method described in example 5. The hexagonal prismatic monocrystals are clearly visible.

This zeolite preserves its crystallinity after calcination under air for one hour at 1000° C.

As silica source, crystalline aluminosilicates such as clays can be utilized. It is also possible to cite the clays of the kaolinite group, such as kaolinite itself and halloysite and the group of montmorillonite.

The general formula of the clays of the kaolinite group is: $Al_2SiO_2O_{10}(OH)_4$. This formula demonstrates a Si/Al ratio equal to 1. In practice, due to the partial substitution of Al by Mg, this ratio varies between 2 and 4, but is lower than the Si/Al ratio of the omega zeolite. It is therefore necessary to add a supplementary silica source to the mother solution.

Among these silica sources can be cited silica gels, colloidal silica, silicic acid, sodium silicate and potassium silicate or mixtures thereof.

Among the metallic oxides can be preferably utilized the metals of which the valency is comprised between 1 and 3, such as alkaline metals, alkaline-earth metals, and rare earth metals. Alkaline metals and particularly sodium are advantageously used.

The organic cations are generally of the tetraalkylammonium type, such as tetramethylammonium (TMA) or tetraethylammonium.

The temperature of the crystallization varies between 10° and 250° C. The formation of the omega zeolite requires a fairly long crystallization time, varying in function of the temperature between 3 hours and 10 days.

The crystallization of the omega zeolite can be carried out in a single step, but it is preferable to utilize the synthesis method known as "germination" (U.S. Pat. No. 3,947,482 assigned to GRACE) since the solid contains less tetraalkylammonium, and is thereby easier to eliminate.

According to this process, a solution A is firstly prepared, containing 2 to 8 moles of a metallic oxide, 0.1 to 2 moles of an organic cation, 2 to 20 moles of silica, 1 mole of alumina and 120 to 400 moles of water. This solution A is maintained for 3 to 200 days at a temperature comprised between 10° and 80° C. Thereafter, 2 to 15% of this solution A is mixed with 85 to 98% of a solution B, containing 1.25 to 16 moles of a metallic oxide, 2 to 40 moles of silica, 1 mole of alumina and 120 to 400 moles of water and preferably 2 to 8 moles of a metallic oxide, 5 to 20 moles of silica, 1 mole of alumina and 120 to 400 moles of water. The mother solution, comprised of solutions A and B is heated in a sealed bulb or ampule, without stirring for 2 to 120 hours between 100° and 200° C.

The omega zeolite formed is thereafter filtered and washed.

The acid form of this zeolite can be utilized as catalyst for the hydration of the olefins and for the isomeric change of the xylenes.

The following examples illustrate the invention, without however in any way limiting the same.

EXAMPLE 1

(Comparative)

(1) A first gel A called nucleation gel having the following stoichiometric composition:

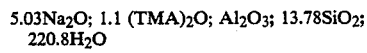

$5.03Na_2O; 1.1 (TMA)_2O; Al_2O_3; 13.78SiO_2; 220.8H_2O$ obtained by mixing:

| | |
|---|---|
| $H_2O$ | 20.6 g |
| NaOH | 1.32 g |
| TMAOH, $5H_2O$ | 2.175 g |
| sodium aluminate | 1.23 g |
| silica | 4.5 g |

This mixture is left to age 117 days at ambient temperature.

(2) A second gel B, called synthesis gel having the same chemical composition as gel A is prepared, without the addition of TMAOH, $5H_2O$.

(3) The mixture containing 90% of freshly prepared gel B and 10% of aged gel A is transferred into a glass bulb. This bulb is sealed and heated without stirring at 136° C. for 8 hours. After washing and drying, the solid obtained presents an X ray diffraction pattern that is characteristic of the omega zeolite without any other crystalline phase.

The measurement of the speed of growth of the crystals during the reaction leads to a value of 12.6 g/h for 100 ml of initial mixture. The chemical analysis of the zeolite corresponds to the molar composition:

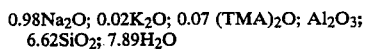

$0.98Na_2O; 0.02K_2O; 0.07 (TMA)_2O; Al_2O_3; 6.62SiO_2; 7.89H_2O$

Figure 1:
FIG. 1 represents a microphotography obtained through using a CAMBRIDGE® electronic scanning microscope with enlargement of 15700 of an omega zeolite prepared according to comparative example 1, from an amorphous alumina source.

In electronic scanning microscopy, the zeolite presents the appearance of beads having an average size of about one micron; these beads are formed of an assembly of crystals of a size of about 0.1 µm (cf. FIG. 1). The thermal stability of this zeolite is estimated by residual crystallinity after calcination under a dry air stream for one hour; the stability obtained, at about 800° C., is comparable to that of the samples previously described (U.S. Pat. No. 4,241,036).

EXAMPLE 2

(1) A first nucleation gel identical to that of example 1 is prepared.

This gel is aged 46 days at 50° C.

(2) A second gel B, called synthesis gel is prepared of the following stoichiometric composition:

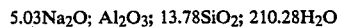

$5.03Na_2O; Al_2O_3; 13.78SiO_2; 210.28H_2O$ from the same components as those for gel A but without the addition of TMAOH, $5H_2O$.

(3) A mixture containing 90% of freshly prepared gel B and 10% of aged gel A is prepared. The mixture is transferred into a glass bulb. This bulb is sealed and heated without stirring for 18 hours at 135° C. After washing and drying, the solid presents a powder diffraction pattern under X-ray characteristic of the omega zeolite, without any other amorphous or crystallized phase.

The measurement of the speed of growth of the crystals during the reaction leads to a value of 9 g/h for 100 ml of initial mixture. The chemical analysis of the zeolite leads to the following chemical composition expressed in oxide moles:

$$0.99Na_2O; 0.06 (TMA)_2O; Al_2O_3; 7.6SiO_2; xH_2O$$

The surface area of the degassed zeolite at 300° C. under vacuum is 215 m$_2$g$^{-1}$. The appearance of the crystals, evaluated by electronic scanning microscopy, shows that the zeolite is in the form of approximately spherical polycrystallines aggregates constituted by small needles of about 0.1 μm.

The thermal stability of the sample has been estimated after heating under dry air stream for 1 hour.

After a heating at 700° C. the zeolite preserves 70% of its crystallinity according to the X-ray diffractogram and its surface area is equal to 150 m$^2$g$^{-1}$. The zeolite becomes amorphous after calcination at 800° C.

The solid is exchanged by ammonium acetate in order to be transformed into omega NH$_4$. This omega NH$_4$ preserves its crystallinity after heating under air at 650° C. and retains 20% of its crystallinity after heating at 750° C.

The fact of increasing the silica content of the network consequently does not allow to substantially improve the thermic stability.

EXAMPLE 3

Synthesis from halloysite as alumina source (1) A gel A having the following stoichiometric composition:

$$3.8Na_2O; 0.2 (TMA)_2O; Al_2O_3; 10SiO_2; 160H_2O$$

from:

| H$_2$O | 20.70 g |
|---|---|
| NaOH | 1.93 g |
| TMAOH, 5H$_2$O | 2.187 g |
| non calcinated halloysite | 1.67 g |
| SiO$_2$ | 3.62 g |

This gel is aged for 178 days at ambient temperature.

(2) A second gel B is prepared having the following composition:

$$3.8Na_2O; Al_2O_3; 10SiO_2; 15H_2O$$

from the same components as for gel A, without the addition of TMAOH, 5H$_2$O.

(3) The same procedure as that described in example 1 is performed and leads to obtention of a solid identified by means of X-ray diffraction as being pure omega zeolite.

EXAMPLE 4

Synthesis from kaolin as alumina source

The procedure and the stoichiometries described in example 3 have been used, with kaolin constituting the clay.

(1) Gel A

| H$_2$O | 20.40 g |
|---|---|
| NaOH | 1.92 g |
| TMAOH 5H$_2$O | 2.175 g |
| kaolin | 1.935 g |
| SiO$_2$ | 3.6 g |

This gel aged for 171 days at ambient temperature.

(2) Gel B: same composition, but without the addition of TMAOH, 5H$_2$O.

(3) After crystallization of a mixture of 90% of gel B and 10% of gel A, aged for 18 hours at 136° C. the solid obtained, characterized by X-ray, is identified as omega zeolite containing kaolin traces. The measurement of the speed of growth of the crystals during the reaction leads to a value of 0.75 g/h for 100 ml of initial mixture. The BET area of the product, after degassing under vacuum at 300° C. is equal to 182 m$^2$g$^{-1}$. After calcination under air at 900° C. the surface area of the zeolite is equal to 209 m$_2$g$^{-1}$ and the crystallinity according to X-ray diffraction is preserved as shown by the spectrum indicated in table 1.

It its ammonium form, the zeolite preserves 50% of its crystallinity after calcination at 750° C.

TABLEAU 1

| d | hkl | I/Io |
|---|---|---|
| 15.767 | 100 | 17 |
| 9.1859 | 110 | 89 |
| 8.0218 | 200 | 15 |
| 6.9424 | 101 | 36 |
| 6.0046 | 210 | 42 |
| 5.5970 | 201 | 11 |
| 5.2852 | 300 | 14 |
| 5.0404 |  | 10 |
| 4.7410 | 211 | 21 |
| 4.4225 | 310 | 18 |
| 3.9725 | 400 | 24 |
| 3.8208 | 002 | 81 |
| 3.7292 | 102 | 36 |
| 3.6390 | 320 | 52 |
| 3.5392 | 112 | 68 |
| 3.4292 | 202 | 28 |
| 3.2686 | 321 | 21 |
| 3.1727 | 500 | 86— |
| 3.1035 | 302 | 37 |
| 3.0475 | 330 | 40 |
| 3.0014 | 420 | 30 |
| 2.9321 | 501 | 100— |
| 2.8732 | 510 | 14 |
| 2.7658 | 421 | 10 |
| 2.6929 | 402 | 12 |
| 2.6618 | 511 | 26 |
| 2.6345 | 322 | 18 |
| 2.5320 | 520 | 15 |
| 2.4925 | 601 | 18 |
| 2.3864 | 332 | 11 |
| 2.2761 | 440 | 14 |

EXAMPLE 5

Synthesis from kaolin as alumina source (1) A gel A having the following stoichiometry:

$$3.2Na_2O; 0.8 (TMA)_2O; Al_2O_3; 10SiO_2; 160H_2O$$

is obtained from:

| | |
|---|---|
| H$_2$O | 61.2 g |
| NaOH | 5.67 g |
| TMAOH, 5H$_2$O | 6.52 g |
| kaolin | 5.805 g |
| silica | 10.8 g |

This gel is aged 64 days at 50° C.

(2) A gel B is prepared in an identical manner but without the addition of TMAOH, 5H$_2$O.

(3) The mixture of 90% of freshly prepared gel B and 10% of aged gel A is crystallized for 13 hours at 160° C.

The solid obtained presents an X-ray diffractogram that is characteristic of pure omega zeolite. The crystals, when examined under electronic scanning microscopy, are present in the form of prismatic monocrystals of 2 to 5 μm long and 0.2 to 1 μm in diameter. The measurement of the speed of growth of the crystals during the reaction leads to a value of 0.43 g/h for 100 ml of initial mixture. The chemical composition expressed in moles is:

0.81Na$_2$O; 0.08 (TMA)$_2$O; 0.04K$_2$O; Al$_2$O$_3$; 5.59SiO$_2$; 447H$_2$O

After calcination at 1000° C. under air for one hour, the zeolite preserves its crystallinity. FIG. 2 shows a microphotograph of these crystals.

EXAMPLE 6

Synthesis from montmorillonite as alumina source (1) A gel A having the following stoechiometry:

3.2Na$_2$O; 0.8 (TMA)$_2$O; Al$_2$O$_3$; 10SiO$_2$; 160H$_2$O is obtained from:

| | |
|---|---|
| H$_2$O | 61.2 g |
| NaOH | 5.76 g |
| TMAOH, 5H$_2$O | 6.52 g |
| montmorillonite | 5.03 g |
| silica | 10.8 g |

This gel is aged 157 days at ambient temperature.

(2) A gel B having the same chemical composition but without the additiion of freshly prepared TMAOH, 5H$_2$O is utilized as synthesis gel: 90% of gel B and 10% of gel A are mixed and this mixture is crystallized at 135° C. for 18 hours without stirring.

After filtration, washing and drying, the obtained solid characterized by X-ray diffraction and electronic microscopy, is identified as a mixture of omega zeolite and non-transformed montmorillonite. The zeolite is present in the form of hexagonal prismatic crystals of irregular size from 0.8 to 2 μm in edge and 1 to 2 μm in length.

EXAMPLE 7

Synthesis from kaolin and utilization of omega zeolite obtained for hydration of the isopentenes (1) A gel A identical to that of example 5 is aged 27 days at 50° C.

(2) A gel B of composition:

3.2Na$_2$O; Al$_2$O$_3$; 14SiO$_2$; 160H$_2$O is obtained from:

| | |
|---|---|
| H$_2$O | 408.00 g |
| NaOH | 37.52 g |
| kaolin | 37.76 g |
| silica | 105.40 g |

(3) A mixture containing 13% of aged gel A and 87% of gel B is crystallized under stirring for 166 hours at 125° C.

The solid obtained after washing and drying presents an X-ray diffractogram characteristic of omega zeolite with a non transformed kaolin rest. The zeolite crystals are present in the form of hexagonal prisms of about 0.1 μm in diameter and 0.2 to 0.5 μm in length.

The measurement of the speed of growth of the crystals during the reaction leads to a value of 0.9 g/h for 100 ml of initial mixture.

(4) The zeolite thus obtained is put into the acid form through intensive exchange with ammonium acetate followed by calcination at 700° C. under air. The resulting solid preserves 70% of the crystallinity of the initial product evaluated according to the evolution of the X-ray spectrum.

(5) The catalytic activity has been evaluated for the hydration of isopentenes in a static reactor of 110 cm$^3$ capacity at 250° C., under 65 atmospheres of total pressure and with a water/olefin ratio of 4.5, the zeolite (0.5 g) being in suspension in the reactional mixture. After 2 hours of reaction, a conversion of 2.5% into methyl-2-butanol-2 is obtained, which corresponds to 48% of the thermodynamic equilibrium. The selectivity is 100% in alcohol.

EXAMPLE 8

Utilization of the omega zeolite in example 7 with isomerization of metaxylene

A physical mixture containing zeolite in the acid form and a hydrogenating function introduced in the form of a Pt/Al$_2$O$_3$ catalyst was tested in the isomeric change reaction of a charge comprising 20% ethyl benzene and 80% metaxylene under the following conditions:

| | |
|---|---|
| P$_{H2}$ | 1 atmosphere |
| temperature | 350° C. |
| H$_2$/hydrocarbon | 500 |
| spatial velocity | 4 h$^{-1}$ |
| catalyst containing 0 2% Pt by weight | |

The composition of the products at the issue of the reactor is:

| | |
|---|---|
| benzene | 0.3% |
| methylcyclohexane | 0.3% |
| toluene | 0.6% |
| ethylbenzene | 11.4% |
| paraxylene | 15% |
| metaxylene | 50.5% |
| orthoxylene | 18.5% |

It will thus be noted that for a metaxylene conversion rate of 35%, the selectivity in paraxylene is 42% and there is no transalkylation in trimethylbenzene.

We claim:

1. A process for the synthesis of the zeolite of claim 1 which comprises: forming a mixture comprised of:

(1) from 2 to 15% by weight of a mixture A containing in molar proportions:

$2\text{-}8M_{2/n}O; 0.1\text{-}2Z_2O; Al_2O_3; 2\text{-}20SiO_2; 120\text{-}400H_2O$ which has been maintained for from 3 to 200 days at a temperature of from 10° to 80° C. and, (2) from 85 to 98% by weight of a mixture B containing in molar proportions:

$1.25\text{-}16M_{2/n}O; Al_2O_3; 5\text{-}20SiO_2; 120\text{-}400H_2O$, wherein:

M is a metal of valency n: Z is an organic cation, and wherein the alumina source is a crystalline aluminosilicate at least one part of which is in suspension in the mixture, and wherein the size of the crystalline aluminosilicate particles in suspension is comprised between 0.5 and 100 μm;

maintaining the mixture at between 10 and 250° C. to form the zeolite at a speed of growth of the crystals lower than 9 g/h for 100 ml of the mixture.

2. A process of claim 1 wherein the aluminosilicate particles in suspension are from 1 to 10 μm.

3. A process of claim 1 wherein the mixture is maintained at a temperature of from 100°–250° C. for from 2 hours to 10 days.

4. A process of claim 1 wherein mixture contains: $2\text{-}8M_{2/n}; Al_2O_3; 5\text{-}20SiO_2; 120\text{-}400H_2O$.

5. A process of claim 4 wherein the mixture is maintained at a temperature of from 100°–200° C.

6. A process of claim 1 wherein the crystalline aluminosilicate is a clay.

7. A process of claim 6 wherein the clay is selected from the family of kaolins.

8. A process of claim 6 wherein the clay is a clay from the montmorillonite family.

9. A process of claim 1 wherein valency n is from 1–3 inclusive.

10. A process of claim 1 wherein M is an alkali metal.

11. A process of claim 1 wherein M is sodium.

12. A process of claim 1 wherein Z is a quaternary ammonium cation.

13. A process of claim 12 wherein the quaternary ammonium cation is a tetraalkyl ammonium cation.

14. A process of claim 1 wherein Z is a quaternary ammonium cation.

15. A process of claim 14 wherein the quaternary ammonium cation is selected from the group consisting of tetramethyl ammonium and tetraethyl ammonium.

16. A process of claim 1 wherein the mixture is maintained at from 100° to 250° C. without mixing.

17. A process of claim 1 wherein the mixture is agitated while maintained at a temperature of from 100° to 250° C.

18. A process for the synthesis of a zeolite having a high thermal stability, having after calcination under air at 900° C. the X-ray powder diffractogram of omega zeolite, wherein when observed under electronic scanning microscopy its crystals are present in the form of scored or plane hexagonal faces of 0.1 to 5 μm in edge and of 0.5 to 5 μm in length, and wherein said zeolite preserves its crystallinity after heating under air for one hour at 1000° C., said process comprising the steps of:

(a) maintaining a mixture A containing in molar proportions:

$2\text{-}8M_{2/n}O; 0.1\text{-}2Z_2O; Al_2O_3; 2\text{-}20SiO_2; 120\text{-}400H_2O$ for a period of from 3 to 200 days at a temperature of from 10° to 80° C.;

(b) preparing a mixture B containing in molar proportions:

$1.25\text{-}16M_{2/n}O; Al_2O_3; 5\text{-}20SiO_2; 120\text{-}400H_2O$, wherein M is a metal of valency n and Z is an organic cation;

(c) forming a mother solution comprised of:
from 2 to 15% by weight of a mixture A, and
from 85 to 98% by weight of a mixture B, wherein the alumina source is a crystalline aluminosilicate at least one part of which is in suspension in said mother solution, and wherein the size of the crystalline aluminosilicate particles in suspension is comprised between 0.5 and 100 μm; and (d) maintaining said mother solution at a temperature between 100° and 250° C. to form the zeolite at a speed of growth of the crystals lower than 9 g/h for 100 ml of the mixture.

19. The zeolite prepared by the process of claim 18.

20. Zeolite having a high thermal stability, having after calcination under air at 900° C. the X-ray powder diffractogram of omega zeolite, wherein when observed under electronic scanning microscopy its crystals are present in the form of scored or plane hexagonal faces of 0.1 to 5 μm in edge and of 0.5 to 5 μm in length, and wherein said zeolite preserves its crystallinity after heating under air for one hour at 1000° C.

* * * * *

UNITED STATES PATENT AND TRADEMARK OFFICE
CERTIFICATE OF CORRECTION

PATENT NO. : 4,891,200

DATED : January 2, 1990

INVENTOR(S) : Francois Fajula, et al

It is certified that error appears in the above-identified patent and that said Letters Patent is hereby corrected as shown below:

Title page:

Item [73] changes assignees to read as follows:

Centre National de la Recherche
Scientifique, Paris;
Elf France, Courbevoie;

Institut Francais du Petrole, Rueil
Malmaison Cedex, all of France

Claim 1, line 1: change "1" to --20--

Signed and Sealed this

Thirtieth Day of July, 1991

Attest:

HARRY F. MANBECK, JR.

Attesting Officer

Commissioner of Patents and Trademarks